(12) United States Patent
King (10) Patent No.: US 9,253,986 B2
(45) Date of Patent: Feb. 9, 2016

(54) WASH PRODUCT COMPRISING A DISINFECTANT MIXTURE OF SILVER IONS AND NON-DISINFECTANT HYDANTOIN

(75) Inventor: Joseph A. King, Wayzata, MN (US)

(73) Assignee: KING TECHNOLOGY, INC., Hopkins, MN (US)

( * ) Notice: Subject to any disclaimer, the term of this patent is extended or adjusted under 35 U.S.C. 154(b) by 980 days.

(21) Appl. No.: 13/506,159

(22) Filed: Mar. 30, 2012

(65) Prior Publication Data

US 2012/0192363 A1     Aug. 2, 2012

Related U.S. Application Data (63) Continuation-in-part of application No. 12/800,692, filed on May 20, 2010, now Pat. No. 8,591,748, and a continuation-in-part of application No. 12/315,285, filed on Dec. 2, 2008, now Pat. No. 7,875,191, and a continuation-in-part of application No. 11/999,654, filed on Dec. 6, 2007, now Pat. No. 7,501,067, and a continuation-in-part of application No. 10/928,668, filed on Aug. 26, 2004, now Pat. No. 7,347,934, and a continuation-in-part of application No. 12/592,700, filed on Dec. 1, 2009, and a continuation-in-part of application No. 61/201,303, filed on Dec. 8, 2008.

(51) Int. Cl.
*C11D 3/28*      (2006.01)
*C11D 3/48*      (2006.01)
*A01N 59/00*      (2006.01)
*A01N 59/16*      (2006.01)

(52) U.S. Cl.
CPC .............. *A01N 59/00* (2013.01); *A01N 59/16* (2013.01)

(58) Field of Classification Search
CPC .................... C11D 17/0086; C11D 17/00047; C11D 3/28; C11D 3/48; C11D 7/3281; C11D 11/0017
See application file for complete search history.

(56) References Cited

U.S. PATENT DOCUMENTS

2006/0123562 A1*   6/2006   Ghosh et al. ...................... 8/147
2014/0369953 A1*   12/2014   Purschwitz et al. ....... 424/78.36

* cited by examiner

*Primary Examiner* — Charles Boyer
(74) *Attorney, Agent, or Firm* — Jacobson and Johnson LLC (57) ABSTRACT

A wash product and method for both washing and disinfecting articles during a washing cycle where the washing can be done in a conventional washing machine using the combination of a conventional detergent for removing residue from the articles and a source of silver ions and a hydantoin for increasing the level of available silver ions to a level that is greater than the level of available silver ions normally available if the source of silver ions were used without the hydantoin.

18 Claims, 9 Drawing Sheets

FIG. 1

FIG. 8
pH levels at water sampling

| Date | Solution C pH | Solution D pH |
|---|---|---|
| 4/21 | 7.46 | 7.44 |
| 4/28 | 7.43 | 7.41 |
| 5/5 | - | - |
| 5/12 | 7.45 | 7.42 |
| 5/19 | 7.45 | 7.44 |
| 5/26 | 7.42 | 7.44 |
| Average | 7.44 | 7.43 |

FIG. 9
Dissolved silver concentrations

| Date | Solution C Ag(ppb) | Solution D Ag(ppb) | Ratio |
|---|---|---|---|
| Start | Start | Start | Start |
| 4/21 | 4.3 | 2.8 | 2 |
| 4/28 | 17 | 8.7 | 2 |
| 5/5 | 46 | 2.4 | 19 |
| 5/12 | 86 | 2.9 | 30 |
| 5/19 | 140 | 4.0 | 35 |
| 5/26 | 220 | 7.1 | 31 |
| Average | 86 | 4.7 | 18 |

FIG. 10

(STUDY 1: Silver concentration calculated from solubility product product of AgBr.)

| Spa Study | Week | Bromide (ppm) | Bromide (mol/L) | Calculated Silver (mol.L) | Calculated Silver (ppb) | Actual Silver (ppb) |
|---|---|---|---|---|---|---|
| 1 | 1 | 110 | 0.001377 | 3.8862E-10 | 0.04 | BRL |
| | 2 | 120 | 0.001502 | 3.5624E-10 | 0.04 | BRL |
| | 3 | 130 | 0.001627 | 3.2884E-10 | 0.04 | BRL |
| | 4 | 150 | 0.001877 | 2.8499E-10 | 0.03 | BRL |
| | 5 | 140 | 0.001752 | 3.0535E-10 | 0.03 | BRL |
| | 6 | 160 | 0.002002 | 2.6718E-10 | 0.03 | BRL |
| | 7 | 150 | 0.001877 | 2.8499E-10 | 0.03 | BRL |
| DMH added | 8 | 106 | 0.001327 | 4.0329E-10 | 0.04 | BRL |
| | 9 | 101 | 0.001264 | 4.2325E-10 | 0.05 | BRL |
| | 10 | 143 | 0.001790 | 2.9894E-10 | 0.03 | 7.0 |
| | 11 | 36.2 | 0.000453 | 1.1809E-09 | 0.13 | 5.0 |
| | 12 | 130 | 0.001627 | 3.2884E-10 | 0.04 | 5.0 |
| | 13 | 300 | 0.003755 | 1.425E-10 | 0.02 | 5.0 |

BRL- Dissolved silver concentration is below reporting level

FIG. 11

STUDY 2: Silver concentration calculated from solubility product of AgBr.)

| Spa Study | Week | Bromide (ppm) | Bromide (mol/L) | Calculated Silver (mol/L) | Calculated Silver (ppb) | Actual Silver (ppb) |
|---|---|---|---|---|---|---|
| 2<br>DMH added | 1 | 26 | 0.000325 | 1.6442E-09 | 1.18 | BRL |
| | 2 | 90 | 0.001126 | 4.7498E-10 | 0.05 | BRL |
| | 3 | 74 | 0.000926 | 5.7768E-10 | 0.06 | BRL |
| | 4 | 59 | 0.000738 | 7.2455E-10 | 0.08 | BRL |
| | 5 | <10 | NA | NA | NA | 5.0 |
| | 6 | 64 | 0.000801 | 6.6795E-10 | 0.07 | 6.0 |
| | 7 | <10 | NA | NA | NA | BRL |
| | 8 | <10 | NA | NA | NA | 5.0 |

BRL- Dissolved silver concentration is below reporting limit

FIG. 12

(STUDY 3: Silver concentration calculated from solubility product of AgBr)

| Spa Study | Week | Bromide (ppm) | Bromide (mol/L) | Calculated Silver (mol/L) | Calculated Silver (ppb) | Actual Silver (ppb) |
|---|---|---|---|---|---|---|
| 3<br>DMH added | 1 | NA | NA | NA | NA | BRL |
| | 2 | <10 | NA | NA | NA | BRL |
| | 3 | <1 | NA | NA | NA | BRL |
| | 4 | <5 | NA | NA | NA | BRL |
| | 5 | <50 | NA | NA | NA | 5.5 |
| | 6 | <10 | NA | NA | NA | 5.0 |
| | 7 | 57 | 0.00071 | 7.50E-10 | 0.081 | 5.0 |
| | 8 | 5.3 | 0.00007 | 8.07E-09 | 0.870 | 6.0 |
| | 9 | 44 | 0.00055 | 9.72E-10 | 0.105 | 6.5 |

BRL- Dissolved silver concentration is below reporting limit

Dissolved Silver Concentrations

| Date | Solution C (with DMH) Ag(ppb) | Solution D (without DMH) Ag(ppb) | Ratio |
|---|---|---|---|
| Date | Start | Start | Start |
| Week One | 4.3 | 2.8 | 2 |
| Week Two | 17 | 8.7 | 2 |
| Week Three | 46 | 2.4 | 19 |
| Week Four | 86 | 2.9 | 30 |
| Week Five | 140 | 4.0 | 35 |
| Week Six | 220 | 7.1 | 31 |
| Average | 86 | 4.7 | 18 |

WASH PRODUCT COMPRISING A DISINFECTANT MIXTURE OF SILVER IONS AND NON-DISINFECTANT HYDANTOIN

CROSS REFERENCE TO RELATED APPLICATIONS

This application is a continuation in part of application Ser. No. 12/800,692 filed May 20, 2010, which is a continuation in part of application Ser. No. 12/315,285 filed on Dec. 2, 2008, now U.S. Pat. No. 7,875,191 which is a continuation of application Ser. No. 11/999,654, filed on Dec. 5, 2007, now U.S. Pat. No. 7,501,067, which is a division of application Ser. No. 10/928,668, filed Aug. 26, 2004 now U.S. Pat. No. 7,347,934 and a continuation in part of application Ser. No. 12/592,700 filed Dec. 1, 2009 which claims priority from provisional application 61/201,303 filed Dec. 8, 2009.

STATEMENT REGARDING FEDERALLY SPONSORED RESEARCH OR DEVELOPMENT

None

REFERENCE TO A MICROFICHE APPENDIX

None

BACKGROUND OF THE INVENTION

The concept of a washing machine having a tub for holding a body of water and soiled laundry therein is known in the art. Typically, during a laundry cycle one dispenses a detergent such as a laundry detergent into the body of water where an agitator swishes the water and soiled laundry back and forth to remove the soil from soiled laundry. Sometimes a disinfectant, such as bleach may be dispensed into the water to disinfect the laundry during the laundry cycle. However, a disadvantage of the use a disinfectant such as bleach is that it may cause damage to the laundry and can injure a person if not handled properly.

Another method of both cleaning and disinfecting during a laundry cycle uses a specialized washing machine for both cleaning and sanitizing laundry. The specialized washing machine, which is shown in U.S. Pat. No. 7,322,065, instead of using a bleach to disinfect, uses a detergent and colloidal silver to wash and disinfect a batch of soiled laundry. The specialized washing machine includes a tub to hold the water and the soiled laundry as well as two silver plates to generate colloidal silver. A voltage, which is applied to the plates, produces the appropriate concentration of colloidal silver in the washing machine with the colloidal silver acting as a disinfectant while the detergent removes the soil from the laundry. The insitu generation of colloidal silver in the washing machine allows the laundry to be both cleaned and disinfected at the same time. However, such systems are both complex and costly since the washing machine requires a set of electrodes as well as a system for controlling the voltage to the electrodes in order to generate sufficient colloidal silver to disinfect the laundry since a sufficient level of silver ions must be generated in the water in order to disinfect the laundry during the laundry cycle.

Another type of well-known washing machine is the dishwasher which typically contains racks for holding soiled dishes while a dishwasher detergent, which is dissolved in wash water, is sprayed on the dishes to remove any residue on the dishes. In some cases one may want to also sterilize or disinfect the dishes. One way of sterilizing or disinfecting is to send the dishes through a high temperature cycle that is sufficient to kill harmful organisms, however, such systems may have adverse effects on the dishes. In other systems a disinfectant may be added to the dishwasher detergent.

The above concepts of sanitizing and disinfectant an article during a washing cycle requires either a special washing machine or the use of disinfectants or heat that may damage the articles whereas the invention described herein comprise a detergent product that can be safely used in a conventional washing machine or dishwasher. While heavy metals such as silver are known as disinfectants unfortunately one of the disadvantages of using a chemical source of silver ions is that the level of available silver ions for disinfecting the articles may be limited by the solubility of silver in the wash water thus creating conditions wherein the articles are not sufficiently disinfected or sanitized since insufficient silver ions are present to sanitized or disinfect the articles.

SUMMARY OF THE INVENTION

A wash product and method for both washing and disinfecting articles such as a batch of laundry or a batch of dishes during a washing cycle where the washing can be done in a conventional washing machine using the combination of a conventional detergent for removing residue from the articles and a source of silver ions and a hydantoin wherein the hydantoin increases the level of available silver ions to a level that is greater than the level of available silver ions normally available if the source of silver ions were used without the hydantoin to thereby enable the articles to be both cleaned and disinfected during the normal wash cycle in a conventional laundry washing machine or a conventional dishwashing machine.

DESCRIPTION OF THE PREFERRED EMBODIMENT

Figure 1:
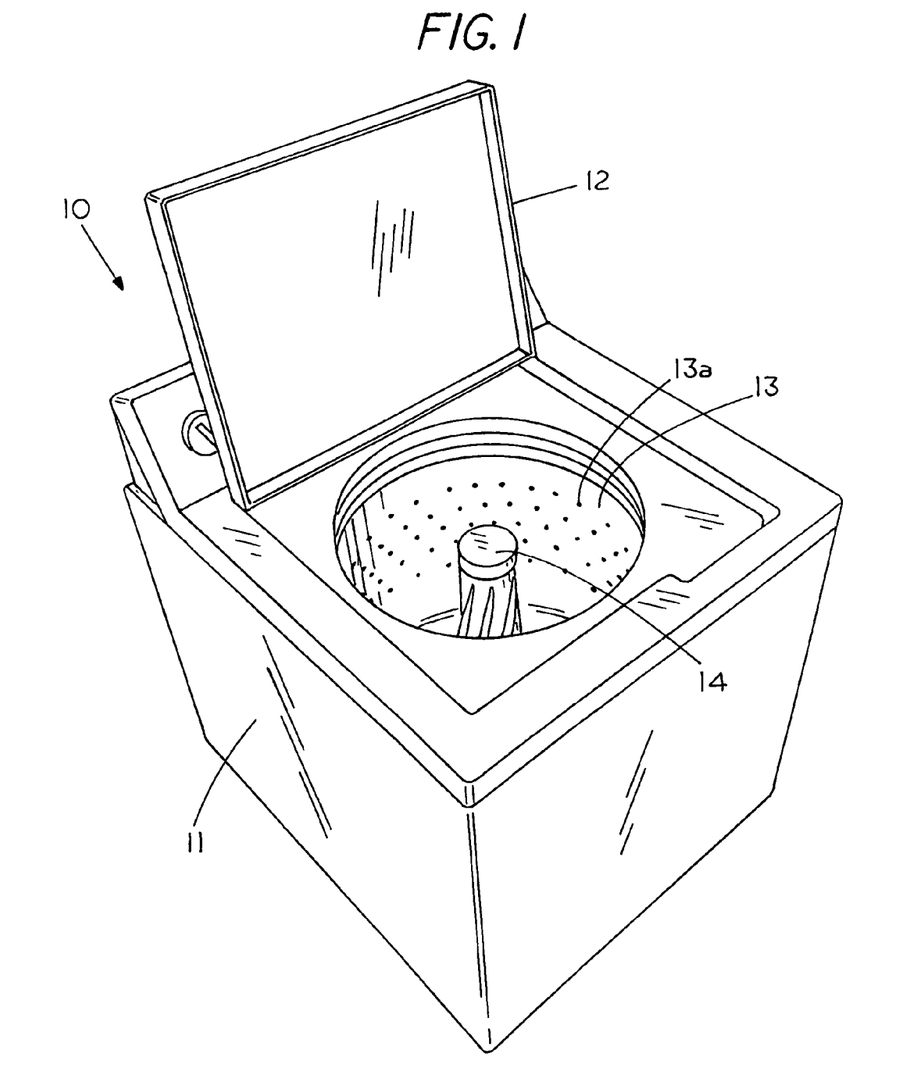
FIG. 1 shows a perspective view of a conventional clothes washing machine.

FIG. 1 shows a perspective view of an example of a conventional clothes washing machine 10 having an outer cabinet 11 and a lid 12. Located beneath the lid is an inner wall of a tub 13 having a set of circumferential openings 13. An agitator 14, which is located in the center of tub 13, is powered by a motor (not shown).

As used herein the term conventional clothes washing machine are those machines that rely on agitation of a batch of laundry, which is located in a container of water containing a detergent, to remove unwanted soil from the laundry and the washing machines does not have features for disinfecting the laundry during the washing cycle. The term detergent or wash detergent as used herein includes those standalone compositions or washing agents that dissolve in water and are generally comprised of soaps and or surfactants that remove unwanted materials from a batch of articles whereas the term laundry product or wash product as used herein includes at least two agents, namely a washing agent such as a detergent and a disinfecting or sanitizing agent wherein each of the agents used during the washing cycle perform a separate but independent function without impeding the function of the other agent and without harming the articles being washed.

Conventional clothes washing machines are well known and are typically used to remove soil or other types of residue from clothes. In some instances clothing or other fabric items may require that not only that the laundry be cleaned but the laundry should also be disinfected. One of the laundry methods includes the addition of a disinfectant such as bleach to the washing machine or alternately one may use a special washing machine that contains a separate disinfection system. Each of such systems may be used to clean and disinfect the laundry, however, the opportunity for damage to the fabrics may occur with the use of bleach. On the other hand the purchase of a specialized washing machine that generates a separate disinfection or sanitizing agent through electrolysis is a costly way of both cleaning and disinfecting a batch of laundry if both cleaning and sanitizing are used only occasionally.

Besides conventional washing machines for washing laundry there also exists conventional washing machine for washing dishes and utensils, oftentimes referred to as dishwashers. Such washing machines are similar in concept except that they contain a rack for statically holding the dishes or utensils while the water with the wash product dissolved therein is sprayed on the dishes and utensils, which are held in the rack. In both applications the water with the detergent is brought into intimate contact with the articles to remove soil or material residue from the articles without harming the articles.

In either case a person who washes articles such as clothes, dishes or utensils may want to also sanitize the articles during the washing cycle with a product that is not harmful to either the articles being washed or the person initiating the washing cycle. Silver ions are known to kill harmful bacteria. One of the disadvantages of the use of a chemical source of silver ions is that level of silver ions which are released into the body of water may be insufficient to kill the harmful organisms since the level of available silver ions in the wash water is inherently limited by the solubility of the silver in the wash water. In the invention described herein the normal level of silver ions available from a chemical source of silver ions is enhanced or increased through the use of a hydantoin, which may or may not have antibacterial properties, but which has been found to increase the level of available silver ions thus allowing one to generate a wash water having a higher concentration of available silver ions which is more effective in quickly killing harmful organisms.

Figure 2:
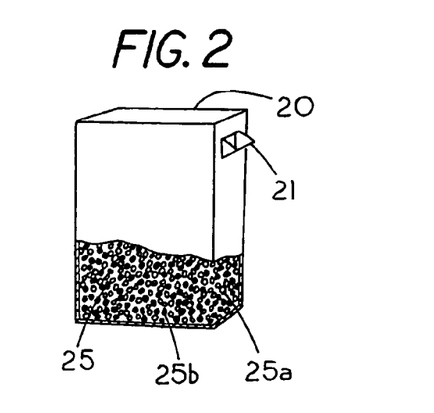
FIG. 2 shows a cutaway view of a dispenser containing a laundry product.
Figure 3:
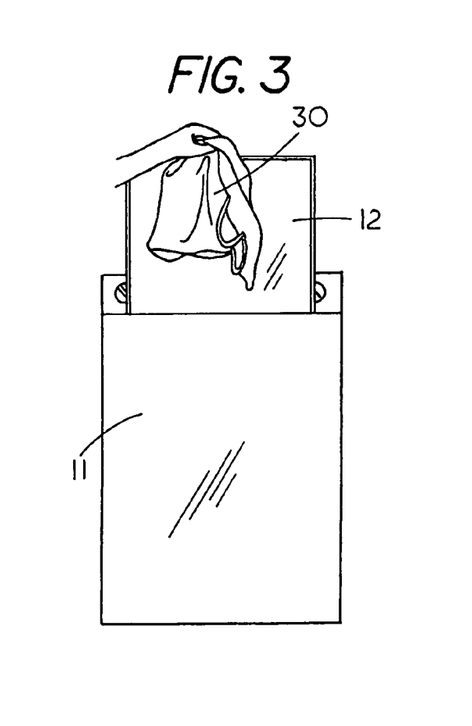
FIG. 3 shows a batch of clothing being placed in the conventional clothes washing machine of FIG. 1.
Figure 4:
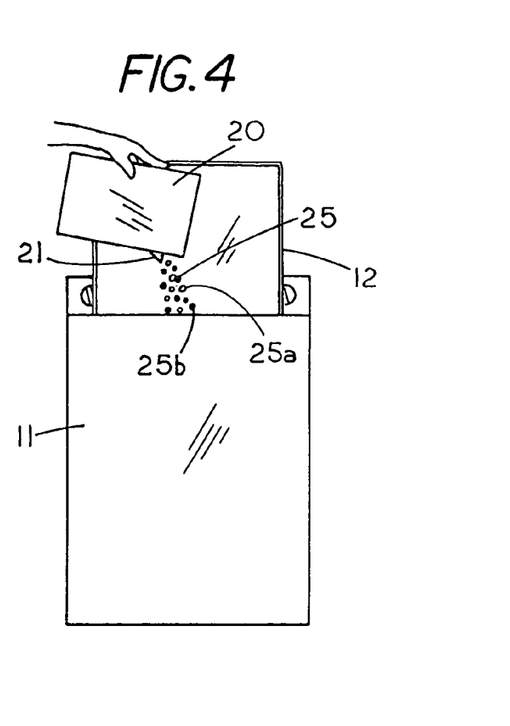
FIG. 4 shows an operator dispensing a laundry product into the washing machine of FIG. 1.

A reference to FIG. 2 shows a cut away view of a typical dispensing container 20 containing a dry laundry product 25 in a pourable condition wherein the dry laundry product can be used for simultaneously washing and sanitizing soiled laundry by addition of the laundry product to a washing machine containing a body of water with the soiled laundry therein. In general, the laundry product 25 may contain any of the commercially available detergents, such as those that contain a conventional soap or surfactant that in the presence of water releases the soil or residue from an article.

In this example the laundry product, which is a both a washing and sanitizing agent, comprises a water activeable laundry detergent 25a in solid dry form for releasing soil or dirt from the soiled laundry and a disinfecting or sanitizing composition 25b. The disinfectant composition 25b comprises a non-disinfectant (i.e. lacking in known sanitizing or disinfecting properties) dimethyl hydantoin (DMH) in solid form which is intermixed with a chemical source of silver ions comprising silver chloride, which is also in solid dry form with the combination intermixed with solid dry particles of laundry detergent to form a laundry product or wash product that both cleans and sanitizes during a wash cycle. The use of silver chloride in a body of water normally maintains a first level of silver ions in the body of water, which is limited by the solubility of the silver ions in the body of water. While silver ions are suitable for disinfecting one of the disadvantages of using silver ions as a disinfectant is that the level of available silver ions in the body of water is relative low and may not be sufficient to properly disinfect the articles during the washing cycle. However, the use of the chemical source of silver ions together with the use of a hydantoin has been found to increase the level of available silver ions in the body of water thereby increasing the ability of the silver ions to disinfect an article during the washing cycle. Thus, the use of the hydantoin in conjunction with the chemical source of silver ions increases the level of available silver ions. In one example the water activeable laundry detergent 25a is in solid form, a hydantoin comprising dimethyl hydantoin (DMH) and the source of silver ions comprising silver chloride are in solid form 25b with the detergent, the source of the silver ions and the hydantoin intermixed and dispensed into the body of water in the washing machine to increase the level of available silver ions in the body of water. Although the dimethyl hydantoin of itself has no known disinfecting properties the dimethyl hydantoin has been found to increase the level of available silver ions in the body of water. By increasing the level of available silver ions in the body of water one increases the disinfecting capability of the composition enabling the disinfecting and sanitizing of articles during a normal wash cycle. In one example the laundry detergent compositions are dry water activeable materials; however, the compositions may be in other forms including liquids or gels or mixtures thereof and other forms of silver such as nano silver particles may be used for the source of ions.

While the laundry product has been described in regard to a dispenser 20 for use in washing clothing the dispenser 20 may also be used for a washing product which contains a dishwashing detergent that may be used in a conventional washing machine such as a dishwasher. In the above example the detergent and the source of silver ions remain in an inactive state in the container. Once the detergent contacts the water the detergent begins to dissolve and the source of silver ions begins to release silver ions into the body of water. Without the presence of the hydantoin the level of available silver ions would be limited by the solubility of the silver ions in the body of water. However, with the presence of a hydantoin, which may or may not have any antibacterial properties, the level of available silver ions increases thus enabling the simultaneous disinfecting and washing of the articles during a washing cycle.

The FIGS. 1-7 illustrate one method of simultaneously washing and disinfecting a batch of soiled laundry 30 in a conventional washing machine 10 comprising the steps of placing the batch of soiled laundry 30 into the conventional washing machine 10 having a tub 13 and an agitator 14. In this example one fills the tub with water and dispenses a laundry product 25 containing a detergent 25a and a chemical source of silver ions and a hydantoin 25b into the body of water. In the next step one initiates the wash cycle to simultaneously wash and disinfect the batch of laundry in the conventional washing machine, which can be done without the aid of a disinfectant such as a bleach and during the normal washing cycle.

Figure 5:
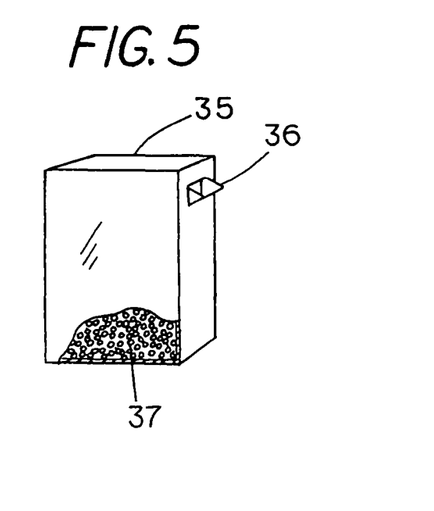
FIG. 5 shows a dispenser containing a laundry detergent and a dispenser containing a disinfectant.
Figure 6:
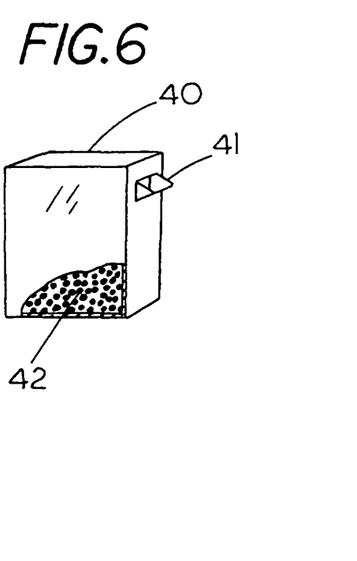
FIG. 6 shows the dispensers of FIG. 5 dispensing detergent and disinfectant into the washing machine of FIG. 1.
Figure 7:
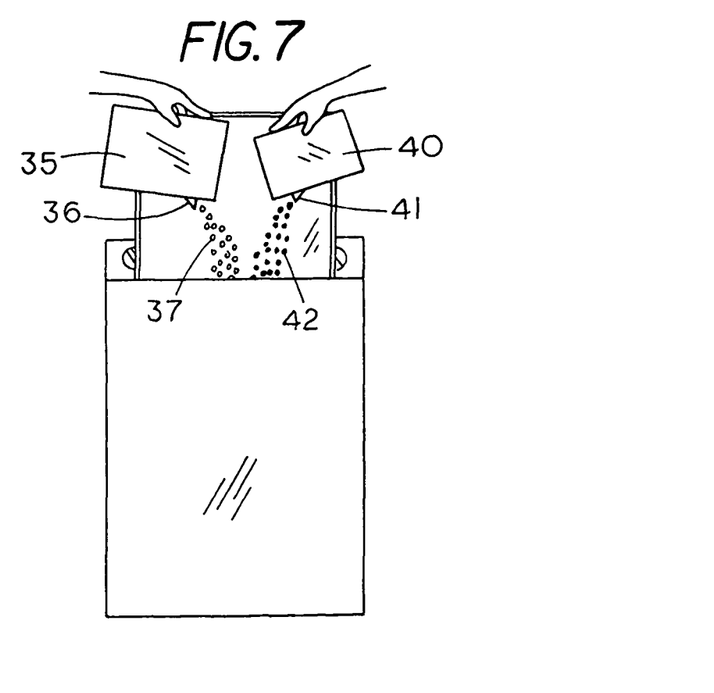

FIG. 5 illustrates an alternate laundry product wherein the laundry detergent 37 is located in a first container 35 having a dispensing spout 36 and the silver chloride and dimethyl hydantoin 42 are located in a second but separate container 40 having a dispensing spout 41. FIG. 6 shows the separate dispensing of the laundry product 37 and the disinfectant 42 into the conventional washing machine. This option allows for the user the option to select the batch of articles to be disinfected.

While the wash product has been desired in relation to washing a batch of soiled laundry the wash product may also be used for cleaning dishes and utensils in a dishwasher. In either application the wash product for cleaning and sanitizing contains a water activeable standalone detergent for removing soil or the like from a batch of articles; and a source of silver ions and a hydantoin wherein the source of silver ions and the standalone detergent may be intermixable with each other to enable simultaneous dispensing of the detergent product composition into a washing machine to enable the water activeable standalone detergent to remove soil and the like from an article while the source of silver ions and the hydantoin coact to sanitize or disinfect the soiled articles during the washing cycle.

As pointed out in the above examples the standalone detergent in the detergent product composition may contain the disinfectant or the disinfectant may be separately dispensed into a conventional washing machine with the detergent product and the disinfectant independently but at the same time each of the agents perform their respective functions to simultaneously clean and sanitize an article during a washing cycle without harming the article. In addition the method using the standalone detergent and the source of silver ions and the hydantoin permits one to simultaneously clean and disinfect the soiled articles in a single cycle in a conventional washing machine.

Thus the wash product may be a detergent and sanitizing product composition comprising the combination of a standalone detergent for removing unwanted materials from a batch of articles and a standalone sanitizer consisting of a hydantoin and a source of silver ions wherein the standalone sanitizer and the standalone detergent are intermixable with each other to enable simultaneous washing and sanitizing of the batch of articles during a washing cycle.

While the preferred example of invention has been described in regard to the chemical source of silver ions comprising silver chloride and, dimethyl hydantoin other hydantoins and other chemical sources of silver may be used without departing from the spirit and scope of the invention as pointed out by the following discussion of test results as shown in relation to FIG. 8 to FIG. 18 which were conducted in a body of water such as a pool or spa wherein various hydantoins were used to enhance the available silver ions so that a lower concentration of a halogen could be used in conjunction with the source of silver ions.

A compound having a hydantoin ring including unhalogenated hydantoins, such as 5,5-dimethylhydantoin (DMH), has the qualities to interact with metal ion donors including silver metal ion donors such as the silver bromide to increase the solubility of the silver bromide in a water environment and aid in the disinfection process. That is, with a silver ion donor in the presence of DMH, the dissolved silver concentrations are higher than anticipated when compared to a control solution without the presence of DMH. The results suggested that DMH interacts with silver to form a soluble complex even if the source(s) of silver are from insoluble salts such as silver bromide, which in some cases may be derived from silver chloride.

In order to verify that the DMH interacts to increase the solubility of extremely insoluble silver, the following tests were performed using either silver chloride or silver bromide as the donor of metal ions in order to demonstrate the enhancement of a silver concentration in a body of water when DMH is used in combination.

Example 1

Silver bromide was initially prepared from a saturated sodium bromide solution, combined with silver nitrate in solution. The yellow precipitate, silver bromide, was than purified by filtration and washing. Additionally, the solid was allowed to dry before use.

A buffer system having a pH of 7.41 was prepared by adding Fisherbrand® potassium phosphate monobasic-sodium phosphate dibasic buffer to 2 Erlenmeyer flasks filled with 1000 ml of purified water. The first flask was treated with 1.12 grams of 5,5-dimethylhydantoin (DMH) and marked solution "D" and the second flask was left untreated and marked solution "C" for control. In regards to the 5,5-dimethylhydantoin (DMH), the 5,5-dimethylhydantoin (DMH) comprised 97% reagent grade was obtained from Aldrich® (CAS No. 77-71-4, Cat. No. D161403-1KG).

After the initial set-up, approximately 0.10 grams of dried silver bromide was introduced into a dialysis tubing (Fisherbrand®, 45 mm, MWCO 12,000-14,000) along with purified water. The ends of the dialysis tubing were clamped to contain the silver bromide and purified water. Next, the outside of the dialysis tubing was rinsed several times to ensure that silver bromide residue was not on the outside of the dialysis tubing. A string was then tied to one clamp, and one tube was introduced into each flask. A magnetic stir bar was used to mix the solutions.

During the period of the test, a 100 ml sample were removed from solution "D" and solution "C" at weekly intervals and analyzed for their pH using Orin Perphect Meter 370 and analyzed for their silver ion concentrations using atomic absorption spectrometry.

Figure 8:
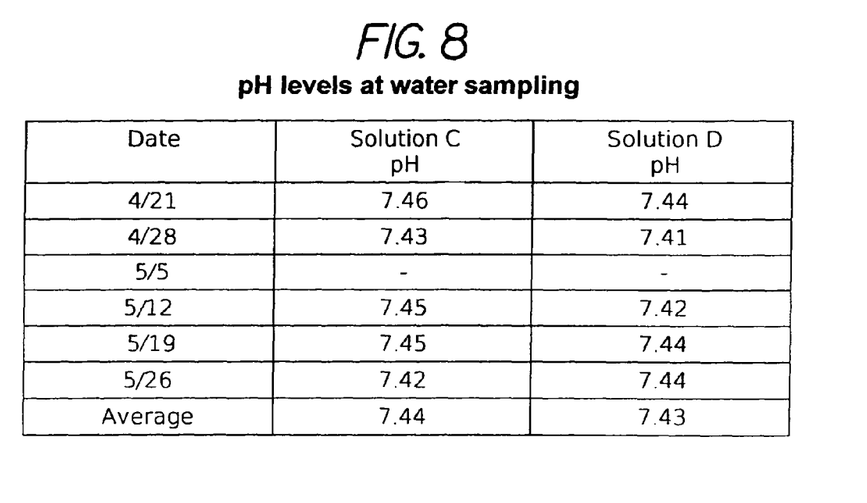
FIG. 8 shows a table of the pH levels of a solution containing DMH and a solution without DMH at weekly time intervals.

FIG. 8 shows a table containing a list of the pH levels obtained from the 100 ml samples for both solution "D" and solution "C" at each of their respective weekly time intervals. It is noted that the preferred pH level for recreational water used in spas, pools, swimming pools, jetted bathtubs and other confined bodies of water is between 7.20 to 7.60 and that the mean value of the pH level measured during the length of the test for both solution "D" and solution "C" was around 7.4, which is within the preferred range.

Figure 9:
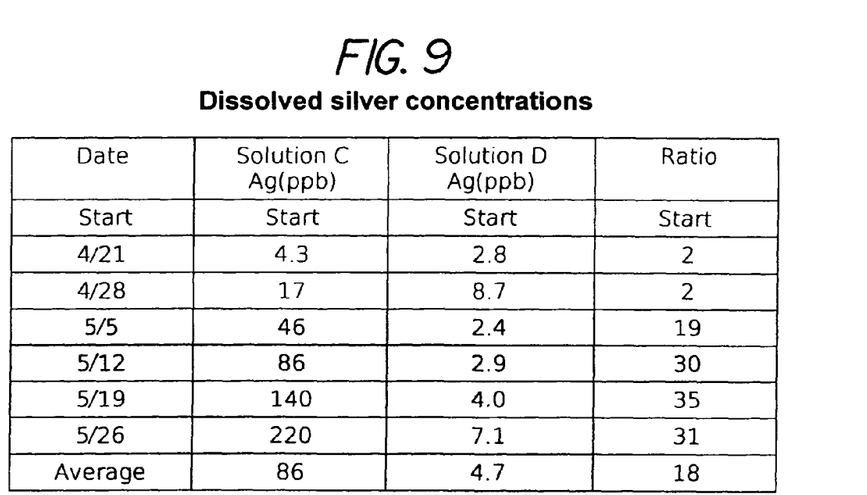
FIG. 9 shows a table of the dissolved silver concentrations of a solution containing DMH and a solution without DMH.

FIG. 9 shows a table containing a list of the dissolved silver concentration, in parts per billion (ppb) obtained from the 100 ml samples for solution "D" and solution "C" at each of their respective weekly time intervals. The average concentration of dissolved silver for solution "D", which contained the DMH, was 86 ppb while solution "C", containing no DMH, had an average concentration of dissolved silver of 4.7 ppb.

A week after the start date, the concentration of dissolved silver for solution D was at 4.3 ppb, while the concentration of dissolved silver for solution C was at 2.8 ppb. By the end of the testing, 6 weeks later, the concentration of dissolved silver for solution D had increase to 220 ppb, while the concentration of dissolved silver for solution C was 7.1 ppb. That is, by the end of the 6 weeks test, the concentration of dissolved silver was at least 30-fold greater in solution D containing the DMH then for solution C containing no DMH.

In summary, the results of the above testing confirmed that in a solution containing silver bromide, the presence of DMH leads to a higher dissolved silver concentrations than compared to a control solution containing silver bromide without the presence of the DMH. These results suggest that DMH interacts with silver to form a soluble complex even if the source of silver comprises an extremely insoluble silver salt such as silver bromide.

Example 2

In the second test, two test spas were used in performing 3 studies to evaluate the potential use of DMH to increase silver solubility in the presence of alternative disinfection systems such as sodium bromide. The first spa used was a 125-gallon Marquis® brand triangle shaped spa having the dimensions 60"×60"×82" with a height of 32" and a water depth of 27" without bathers. This spa featured 13 jets and one pleated filter cartridge (Unicel 5CH-502), having a filtration area of 50 square feet. The second spa was a 325-gallon Dimension One® brand spa having the dimensions 90"×90"×35.5" with a water depth of approximately 25" without bathers. The Dimension One® brand spa featured 32 jets and two pleated filter cartridges (Unicel 7CH-975), each having a filtration area of 75 square feet. Spa water was maintained between 100° F. (37.8° C.) to 104° F. (40° C.) and was circulated at least 2 hours daily.

In the each of the studies, a reagent grade Dimethylhydantoin (DMH, CAS No. 77-71-4) obtained from Aldrich® with a 97% purity, was used. A concentration of 5 ppm DMH was selected because that amount of DMH can be delivered in the existing King Technology, Inc. Spa Frog® Mineral Cartridge to a 600 gallon spa, the largest volume for the cartridge was designed.

The source of silver ions was obtained from a King Technology Inc. Spa Frog® Mineral Cartridge, which was randomly selected from King Technology Inc.'s production inventories for use in these studies and installed into the in-line system on the spa. These mineral cartridges release silver ions into the spa in the form of silver chloride.

In Spa Studies 1 (FIG. 10) and spa study 2 (FIG. 11), a commercially available sodium bromide disinfectant system (Rendezvous®) was used. With this bromine disinfectant system, the sodium bromide solution is oxidized by the addition of potassium peroxymonosulfate.

For Spa Study 3 (FIG. 12), different sodium bromide disinfecting systems were evaluated in two phases. During the first phase, the commercially available sodium bromide oxidized by the sodium dichloro-s-triazinetroine disinfectant known as Spa Essentials® Brominating Concentrate was used. For the second phase of the spa study reagent grade sodium bromide salt and potassium peroxymonosulfate was used.

During the study, the test spa was filled with fresh water prior to the initiation of each study and the water balanced according to Taylor Technologies Pool & Spa Water Chemistry Manual. The pH was reduced through the addition of sodium bisulfate (pH Down Balancer, GLB, Alpharetta, Ga.) to a range from 7.2 to 8.0. After balancing the spa the King technology, Inc. Spa Frog® Mineral Cartridge was installed into the inline system of the test spa and a source of bromine was added to the spa water.

In Spa Study 1 an amount of DMH was added to the spa water after 7 weeks of silver data had been collected to result in a final concentration of 5 ppm. For Spa study 2, an amount of DMH was added to the spa water after 3 weeks of silver data had been collected to result in a final concentration of 5 ppm, and for Spa Study 3 an amount of DMH was added to the spa water after 1 week of silver data had been collected to result in a final concentration of 5 ppm.

Sodium bromide or brominating concentrate (dichloro-striazinetrione plus sodium bromide) was added to each spa during test intervals. Typically, sodium bromide was activated by oxidation to bromine with potassium peroxymonosulfate. Alternatively, when the brominating concentrate (dichloro-striazinetrione plus sodium bromide) was used, the sodium dichloro-s-triazinetrione oxidized the sodium bromide to make bromine in-situ. Additional water was added to the spa when the water level dropped below the skimmer water returns.

Figure 10:
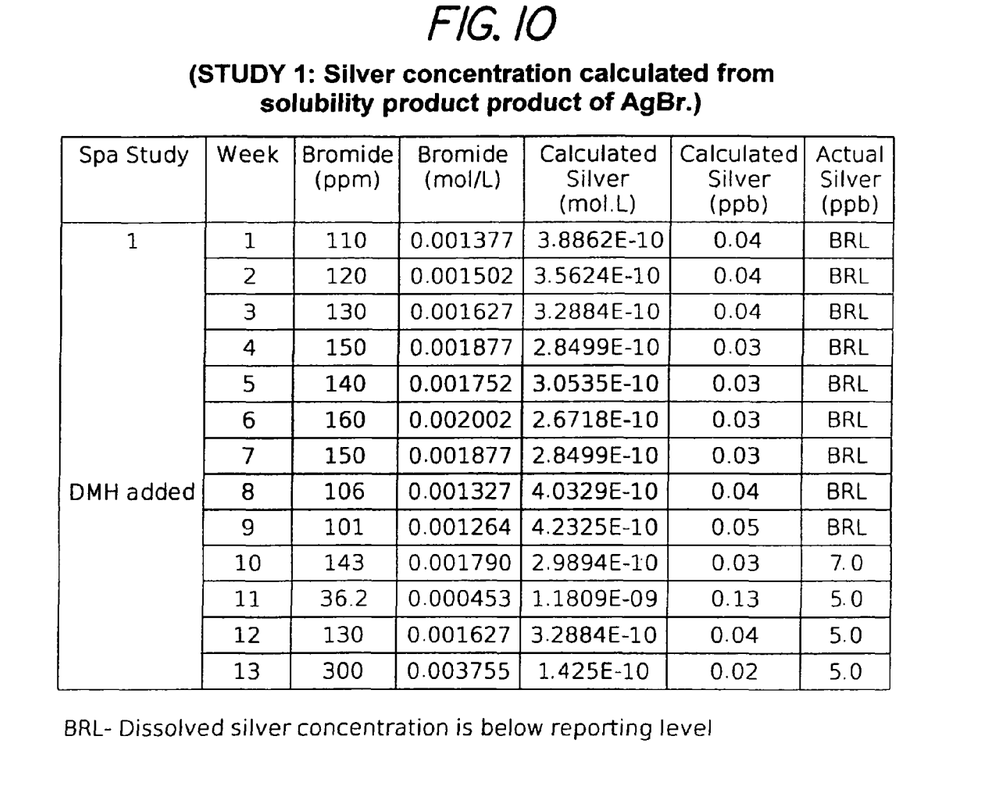
FIG. 10 shows a table containing the test results for bromide and dissolved silver concentration for Spa Study 1.
Figure 11:
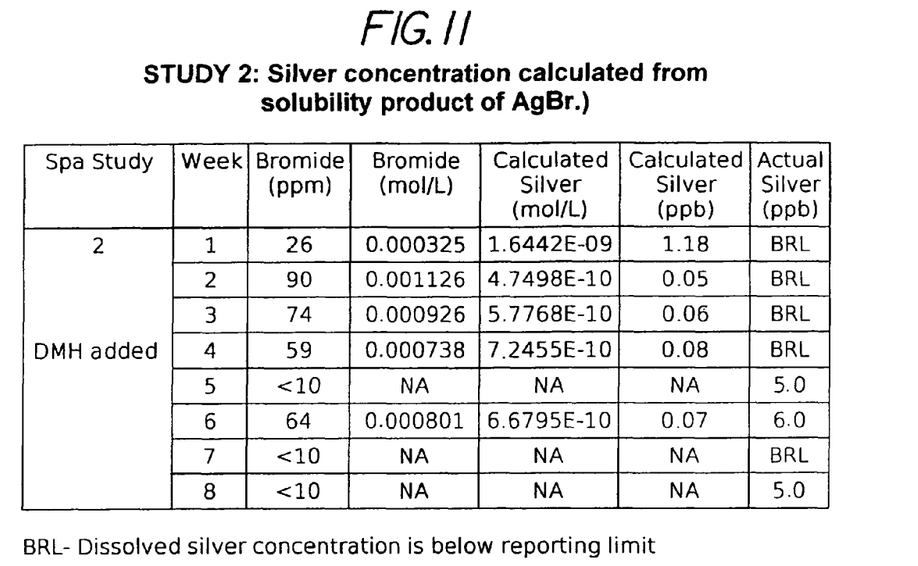
FIG. 11 shows a table containing the test results for bromide and dissolved silver concentration for Spa Study 2.
Figure 12:
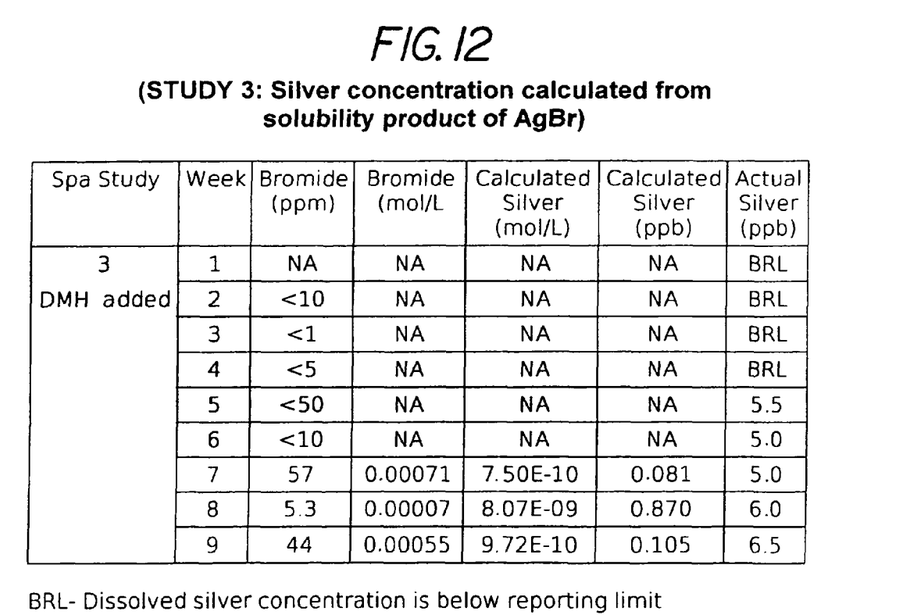
FIG. 12 shows a table containing the test results for bromide and dissolved silver concentration for Spa Study 3.

Chemical tests were performed with water samples obtained from each of the spa for dissolved silver, bromide, and chloride approximately once a week. Bromide was tested to provide a means to calculate the theoretical silver concentration based on the solubility product of silver bromide. The spa water samples were each tested for the bromine, and dissolved silver concentration. Result of the test for bromide and dissolved silver concentration are shown in FIG. 10 for Spa Study 1, are shown in FIG. 11 for Spa Study 2, and are shown in FIG. 12 for Spa Study 3.

Additionally, to maintain the water within the spa total alkalinity, turbidity, and pH were tested and maintained within ranges accepted by the industry. The ideal pH for a spa is 7.20 to 7.60, however wider ranges are acceptable. In the studies, the average pH for Spa Study 1 was 7.51, Spa Study 2 showed an average pH of 7.61, and Spa Study 3 had an average pH of 7.47. These three spa studies were maintained within the ideal pH for a spa.

The International Aquatic Foundation (ANSI/NSPI) recommends a level of total bromine to be between 2.0-4.0 ppm for residential spas with a max of 6.0 ppm. In the studies, the average total bromine concentration measured for Spa Study 1 was 3.74 ppm, the average total bromine concentration measured for Spa Study 2 was 6.56 ppm, and the average total bromine concentration measured for Spa Study 3 was 3.58 ppm.

In regards to the level of silver ions, the King Technology, Inc. Spa Frog® Mineral Cartridge provides silver ions in the form of solid silver chloride (AgCl) distributed over a porous matrix. Water flowing through the matrix comes into contact with the AgCl resulting in the release of soluble silver ions to water. DMH was also released into the water resulting in the formation of ionic-hydantoin structures. It would be anticipated that soluble silver ions would be depleted from spa water through the formation of silver bromide, an insoluble salt. However, as shown in FIG. 10 for Study 1, after the DMH was added to the water in the pool, the actual silver concentrations were higher than the calculated theoretical silver concentration.

The result of Study 1 were further supported in Study 2 and Study 3, shown in FIGS. 11 and 12, which both show that after the DMH was added to the water in the pool, the actual silver concentrations were higher than the calculated theoretical silver concentration. More specifically, once measurable within reporting limits the average measured concentration of dissolved silver for Spa Study 1 was 5.5 ppb. Spa Study 2 had an average measured concentration of 5.33 ppb for dissolved silver and the third Spa Study had a measured concentration of dissolved silver of 3.2 ppb. Referring to FIGS. 10, 11, and 12, the highest observed silver concentration in each spa study was, 7 ppb, 6 ppb, and 6.5 ppb, respectively.

Referring to FIGS. 10, 11, and 12, the results of the three spa studies revealed that before the addition of DMH, dissolved silver concentration was below the official reporting limit of 4.8 parts per billion (ppb). However, around one to three weeks after the addition of a concentration of 5 ppm DMH, silver concentrations in each of the Spa Studies increased above the reporting limit, and were significantly higher than concentrations that would be anticipated based on silver solubility calculations from silver bromide. The above results of Spa Studies 1, 2, and 3 thus supports the finding that the combination of an unhalogenated hydantoin such as 5,5-dimethylhydantoin with a metal ion donor such silver bromide enhances a concentration of the metal ions in the body of water by retaining or increasing the solubility of metal ions from other metal ion donors to retain the antimicrobial activity of the metal ions in the water. Generally, a compound contain a hydantoin ring is added as needed with levels of 5 ppm sufficient to provide enhanced silver ion concentration, however, if the compound containing a hydantoin ring is considered inert one may want to maintain the level of at 10 ppm or more in the body of water. For example if, DMH, which is considered inert, may be normally added to maintain a level of 5 ppm DMH, which is sufficient to provide an enhanced silver ion concentration, however since DMH is considered inert one may want to maintain the level of DMH at 10 ppm or more in the body of water to ensure there is sufficient DMH available at all times.

Because the levels of metal ions in the body of water, such as silver ions; are greater than normally expected the amount of halogen used in conjunction with the source of metal ions, such as silver ions, can be reduced as much as 50% to 75% from existing recommendations while still maintaining the water in a sanitized condition.

Figure 13:
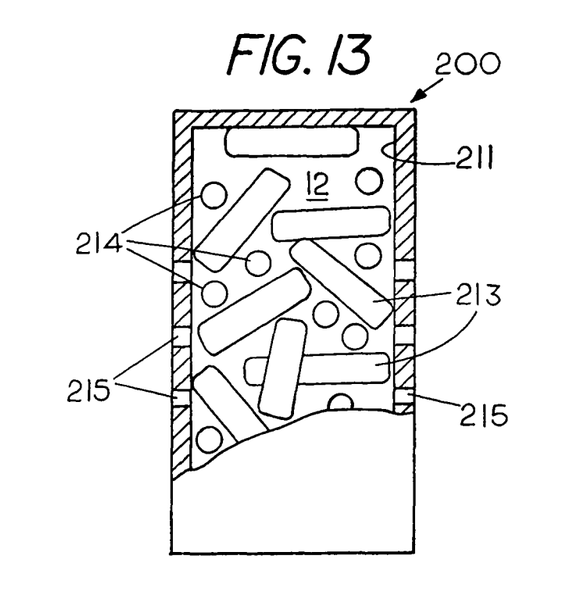
FIG. 13 shows a dispenser having a housing containing a compartment containing DMH and a silver ion donor comprising silver chloride therein.

Referring to FIG. 13 and FIG. 14, FIG. 13 shows an example of a dispenser 200 having a housing 211 containing a compartment 212 therein. Located in compartment 212 is a source of DMH 213 and a bactericide comprising a silver ion donor such as silver chloride 214. A set of openings 215 allows water access to compartment 212 and to the source of DMH 213 and the silver chloride 214.

Figure 14:
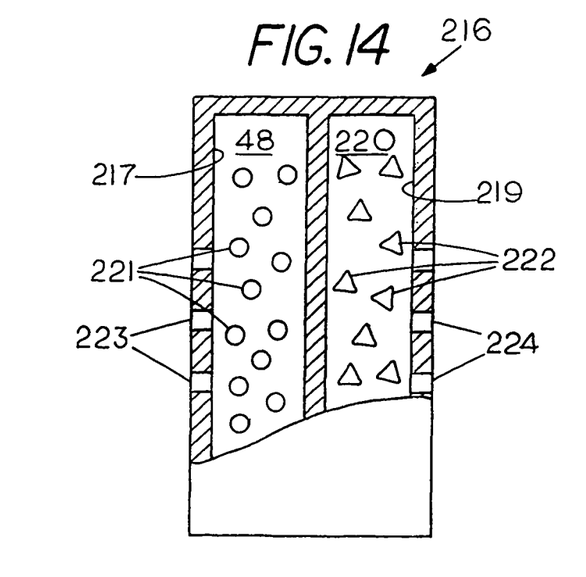
FIG. 14 shows a dispenser having a first housing containing a compound containing a hydantoin ring and a second housing containing silver ion donor comprising silver chloride therein.

FIG. 14 shows an alternative embodiment comprising a dispenser 216 having a first housing 217 containing a compartment 218 and a second housing 219 with a compartment 220 therein. Located in compartment 218 is a silver ion donor such as silver chloride 221 and located in compartment 220 is a source of DMH 222. A set of openings 223 allows water access to compartment 218 and to the silver chloride 221. Similarly, a set of openings 224 allows water access to compartment 220 and the source of DMH 222. It is noted that although FIGS. 13 and 14 shows the use of the silver ion donor as comprising silver chloride, other types of silver ion donors and other alternative bactericides whose solubility can be changed in the presence of DMH can also be used such as silver bromide.

In regards to the source of DMH 213,222 of FIGS. 13 and 14, note that FIG. 13 shows a source of DMH 222 in particle form with the aforementioned particles having an initial size that is larger than the size of opening 223 to prevent the DMH particles from escaping through opening 223. FIG. 13 shows a source of DMH 213 in tablet form. In regards to the DMH tablets, it is noted that various types of material, including but not limited to microcrystalline cellulose (MCC), may be used as a binder in the formation of the DMH tablets which are tabletized with the metal ion donor so that both the DMH and the metal ion donor can be placed in the body of fluid to be treated.

It is also noted that a preferred level of the DMH present in the body of water is between 5 ppm and 25 ppm with the DMH and the source of silver cooperating to maintain a level of silver ions present in the amount of 1 to 3 ppb and/or alternatively cooperating to maintain a level of silver ions present to sustain a standard plate count at 35 degrees F. of less than 200 colonies per milliliter. The level of the compound containing a hydantoin ring can be maintained at relatively low levels and may depend on the hydantoin selected. In some cases a minimum of 5 ppm is sufficient and in other cases may be less depending on the compound containing the hydantoin ring, however, the amount of the compound containing the hydantoin ring may be established by trial and error, particularly if the compound containing the hydantoin ring contains any biocidal properties. In general a level of 5 ppm of the compound containing a hydantoin ring is sufficient if the compound containing the hydantoin ring lacks any biocidal properties.

One can place the dispenser 210,216 containing both the source of DMH 213,222 and the silver chloride 214,221 in the body of water and allowing water to come into contact with the source of DMH 213,222 and the silver chloride 214,221 to periodically release DMH and silver ions into the body of water. As the DMH is released into the body of water, the DMH is carried to the silver chloride 14,221 and interacts with the silver chloride 214,221 to increase the solubility of the silver ions to allow for the release of more silver ions into the body of water than the silver chloride 214,221 alone.

The invention can also include a method of treating a body of water to kill microorganisms by maintaining an effective concentration biocides comprising the steps of: (a) adding a silver salt 214, 221 to the body of water; and (2) adding a concentration 5,5-dimethylhydantoin (DMH) 213, 222 to the body of water to interact with the silver salt 214, 221 to maintain a silver ion concentration effective to kill microorganisms. The aforementioned method can also include the steps of (3) adding silver chloride 214, 221 to the body of water; (4) adding silver bromide to the body of water (5) treating a body of recreational water for at least partial human immersion therein; (6) placing a dispenser 210, 216 containing both the silver salt 214, 221 and the 5,5-dimethylhydantoin 213, 222 in the body of water and allowing water to come into contact with both the silver salt 214, 21 and the 5,5-dimethylhydantoin 213, 222; and (7) adding silver chloride to the body of water on a carrier of limestone.

For example, in a pool system having a pool containing a body of water a halogen generator such as a chlorine generator may be used to maintain a chlorine concentration of between 0.25 ppm to 1 ppm in the body of water while a dispenser containing a source of silver ions and a compound containing a hydantoin ring can be used therewith to maintain the pool in a sanitized condition. Similarly, in a spa system containing a body of water a bromine generator may be used to maintain a lesser bromine concentration in the body of water. While a dispenser containing a halogen and a source of silver ions, a compound containing a hydantoin ring can maintain the pool in a sanitized condition. Thus in systems where halogens are used as part of the sanitizers the level of halogen present in the body of water can be reduced to thereby reduce adverse effects of halogens. The systems described herein provide low cost easy to use systems that are consumer friendly and can be used in an in home spa or swimming pool or the like.

In summary, as FIG. 9 shows, that compounds containing a hydantoin ring, which may not have antibacterial properties such as 5,5-dimethylhydantoin (DMH), can interact with metal ion donors including silver metal ion donors such as silver bromide to increase the solubility of the silver bromide in a supply of water and aid in the sanitation process. For example, it has been found that with a silver ion donor in the presence of DMH in a liquid such as water, the dissolved silver concentrations are higher than anticipated when compared to a control solution without the presence of DMH even though the DMH lacks antimicrobial properties. In addition, the dissolved silver concentration also increases with time. The results suggested that compounds containing a hydantoin ring interact with silver to form a soluble complex even if the source(s) of silver are from insoluble salts such as silver bromide, which in some cases may be derived from silver chloride. It has also been found that compounds that contain a hydantoin ring which do have antimicrobial properties such as halogenated hydantoins including for example, Bromochlorodimethylhydantoin (BCDMH) and Dichlorodimethylhydatoin (DCDMH) also provide for greater availability of metal ions.

In the example described herein the effectiveness of the sanitizing metal ions, particularly the silver ions, is enhanced through increasing the solubility of the silver ions by addition of a compound or compounds containing a hydantoin ring in the presence of water regardless of whether the compound containing a hydantoin ring contains a halogen.

While the body of water which are particularly well suited for the invention are recreation bodies of water other bodies of water such as used for therapeutic or other human external contact may be used with the inventions described herein.

One can maintain a body of water in a sanitized condition by use of either a source of metal ions and a halogen generator generating a minimum halogen level sufficient to maintain the body of water in a sanitized condition or by decreasing the minimum halogen level by as much as 50% to 75% while adding a compound containing a hydantoin ring to the body of water. By sufficient to maintain the body of water in a sanitized condition is understood to mean to render the body of water free of harmful microorganisms as evidenced by tests described herein.

One can employ a method of maintaining a body of water for external human contact in a sanitized condition with use of a halogen and a source of silver ions as the sole sanitizers wherein the halogen is maintained at less than 0.5 ppm if the halogen is chlorine by adding a compound containing a hydantoin ring to the body of water. Similarly the level of bromine can be reduced if used with the compound containing a hydantoin ring and a source of silver ions.

More specifically, the method includes maintaining a body of water for external human contact in a sanitized condition with use of a halogen generator and a source of silver ions as sanitizers by setting the halogen generator to generate between 0.25 and 0.5 ppm in the body of water if the halogen is chlorine and setting the halogen generator to generate less than 2 ppm in the body of water if the halogen is by bromine and adding at least 5 ppm of a compound containing a hydantoin ring to the body of water.

The method may include maintaining a recreational body of water and a level of halogen in the body of recreational water with a halogen generator and the sanitized condition of the body of water is characterized by any or all of the following conditions: (a) an organism count in a recreational body of water of less than 200 bacteria per milliliter; (b) a number of coliform bacteria in the recreational body of water less than 2 organisms per 100 milliliter; or (c) a number of entercoccal organisms in the recreational body of water less than 4 organisms per 100 milliliter.

The method of washing may include maintaining of a body of water in the sanitized condition wherein a halogen and a source of silver ions, which would normally require at least 0.5 ppm of chlorine in conjunction with the source of silver ions, by maintaining the chlorine level at 0.25 ppm to 0.5 ppm and adding a compound contain the hydantoin ring, which may lack sanitizing properties to the body of water.

When a halogen such as bromine is used as a disinfectant in a body of water such as in recreational water used in spas, pools, swimming pools, jetted bathtubs and other confined bodies of water one generally wants to maintain the concentration of the bromine in the range of 3-5 parts per million (ppm). Similarly, when a metal ion is used one generally wants to maintain the concentration of the metal ion in the range of 1-2 ppb. Calculations reveal that when metal ions and bromine are combined the bromine limits the available metal ions in the body of water to levels that are ineffective to control the microorganisms in the body of water.

The amount of bromine and amount of metal ions can be maintained in a body of water at effective levels to kill microorganism and that the combination can be maintained with levels of bromine that are less than if the bromine was used alone. That is, one may use 3-5 ppm of bromine when bromine is used alone but when bromine is used in conjunction with metal ions such as a silver ions one may need only 1-2 ppm of bromine.

In order to verify that the concentration of metal ions and concentration of bromine were maintained at effective levels three different bodies of water were supplied with bromine and a metal ion. The test results are as follows:

Example 3

A cartridge containing a metal ion donor comprising limestone particles with some of the particles having a silver chloride coating was placed in a 300 gallon spa. The limestone particles were used for the carrier while the silver chloride became the silver ion donor. The cartridge contained approximately 57 grams of granular limestone coated with a polymer containing silver chloride. In addition to the silver ion donor bromine was added to the spa from a bromine donor. The bromine level was maintained at 1-2 ppm through the daily addition of a bromine donor comprising 1-bromo-3-chloro-5,5 dimethylhydantion ($C_5H_6BrClN_2O_2$) which is available commercially in granular form under the tradename BromCide®. Approximately 14 grams of 1-bromo-3-chloro-5,5 dimethylhydantion (BCDMH) was added daily to maintain the bromine concentration at levels of 1-2 ppm during bather use. The temperature of the spa was maintained at 102 degrees F. Two bathers used the spa for 30 minutes per day for 5 days per week. The level of silver ions in the spa was measured weekly. It was found that he level of silver ions in the spa ranged from about 1-3 ppb during the test. The pH was maintained in the range of 7.24 to 7.99 during the test.

Water samples were collected at weekly intervals for silver ion analysis. Water collection bottles contained nitric acid as a preservative and after sample collection the samples were maintained at approximately 4 degrees C. until delivered to a contract testing laboratory. Silver ion analyses was performed by Inductively Coupled Plasma Mass Spectrometry. The analysis were presumed to be specific for soluble silver due to the sample preparation steps. The level of bromine in the water was determined using the DPD Spectrophotometer Method. Water samples were collected in 125 ml flasks and 10 ml of the collected water was transferred to sample cells for analysis by HACH Method 8016 (Program 1300) using a HACH DR/4000 spectrophotometer. HACH DPD Total Chlorine Reagent was added to the 10 ml samples in the cells and reacted for three minutes. The results were automatically calculated and reported as mg/L (ppm).

Figure 15:
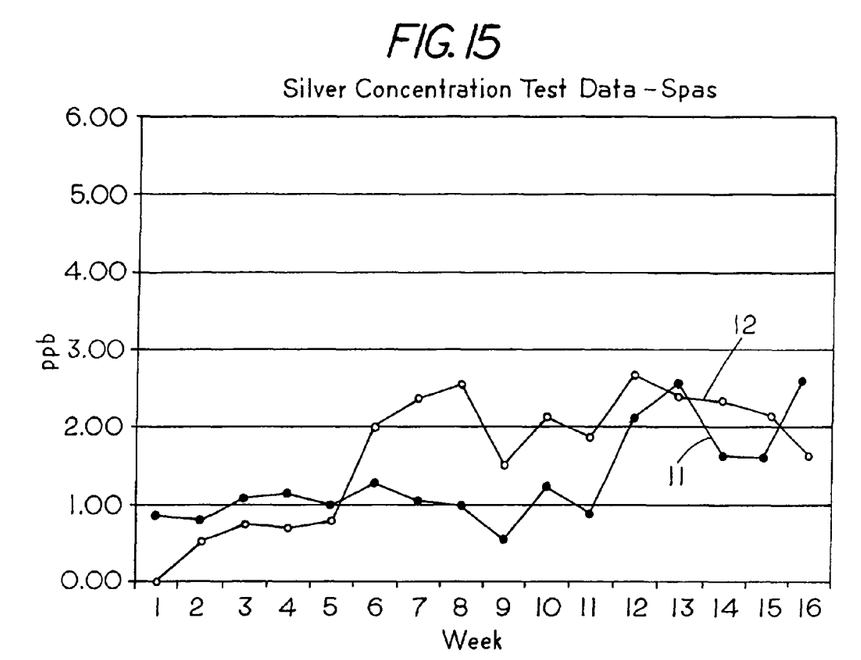
FIG. 15 and is a graph of the levels of silver in a spa as a function of time.

FIG. 15 is a graph of the measured valves of silver ion in a 300 gallon spa and a 550 gallon spa. Reference numeral 11 identifies the silver ion concentration on a weekly basis in the 300 gallon spa and reference numeral 11 identifies the silver ion concentration on a weekly basis in the 550 gallon spa. In both cases the level of bromine was being maintained at a level of 1-2 ppm. As can be seen from the graph, after initial start up the concentration of silver ions ranged from about 1 ppb to 3 ppb. The combination proved effective in killing microorganism and lacked the odor associated with a halogen such as chlorine.

The use of the chelating agent 1-bromo-3-chloro-5,5 dimethylhydantion (BCDMH), which is commercially available under in either gel, solid, granules or tablets form performed a dual purpose since the chelating agent contained the bromine for release into the water as well as preventing the reduction of the level of silver ions. Other chelating agents such as 1,3 dichloro-5,5 dimethylhydantion and 1,3 dibromo-5,5 dimethylhydantion are also suitable for use in the present invention. The use of the chelating agent and particularly a chelating agent with bromine attached to a hydantoin group was found to provide a two part disinfectant or biocide where the levels of bromine could be maintained at effective antimicroorganism levels which were equal or less than the effective antimicroorganism levels of the bromine when used alone. By antimicroorganism levels it is understood to mean that the levels of the biocide are sufficient to kill the microorganisms in the body of water.

While 1-bromo-3-chloro-5,5 dimethylhydantion (BCDMH) is a preferred chelating agent and bromine donor since it carries the bromine attached to a hydantoin group. However, other chelating agents where the bromine is not part of the chelating agent can also be used in conjunction with a separate bromine donor and metal ion donor For example, the use of a bromine donor comprising bromine in stick or other form can be used to release the bromine into the body of water if a separate chelating agent such as anthranilate, saccharinate or sulfadiazine is present in the body of water with the metal ions or a metal ion donor.

Figure 16:
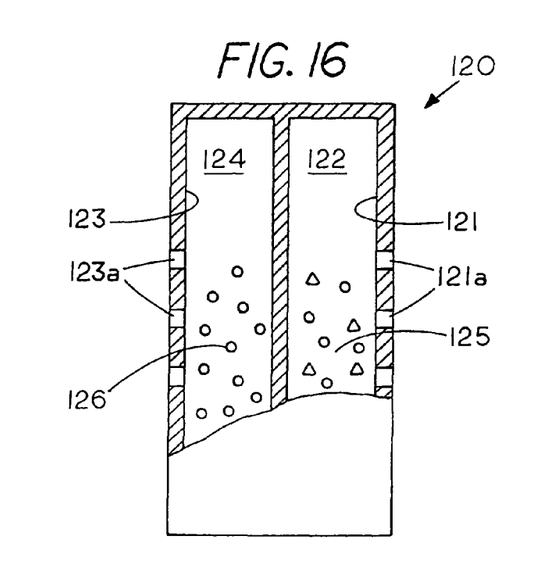
FIG. 16 is a cutaway view of a dispenser containing a bromine donor and a metal ion donor.

FIG. 16 shows a dispenser 120 having a first housing 121 containing a compartment 122 and a second housing 123 with a compartment 124 therein. Located in compartment 122 is a bromine donor 125 and located in compartment 124 is a silver ion donor 126. A set of openings 121a allows water access to compartment 122 and to the bromine donor 125. Similarly, a set of openings 123a allows water access to compartment 124 and the silver ion donor 126. The present invention included step of placing a dispenser 120 container both a bromine donor 125 and a silver ion donor 126 in the body of water and allowing water to come into contact with the bromine donor 125 and the silver ion donor 126 to periodically release bromine and silver ions into the body of water. A measurement of the microbial activity in the body of water demonstrated that with even though the bromine concentrations was less than normally used the combination of the lower bromine and the silver ion produced an effective disinfectant for a body of contained water making it a suitable disinfectant for common recreational bodies of water such as spas and pools. In one example the a chelating agent selected from the group consisting of 1-bromo-3-chloro-5,5dimethylhydantion, 1,3 dichloro-5,5 dimethylhydantion, 1,3 dibromo-5,5 dimethylhydantion, anthranilate, saccharinate and sulfadiazine.

While numerous factors influences the concentration of disinfectants in bodies of water such as pools, spas and the like the EPA provides Efficacy Data Requirements for bodies of water such as Swimming Pool Water Disinfectants which are spelled out in EPA DIS/TSS-12/Apr. 23, 1979, and are herein incorporated by reference. The example described provides a cooperative two component biocide in a body of water that generates bromine and silver ions in concentrations that are effective in maintaining the microorganisms at levels below the unacceptable levels specified in EPA DIS/TSS-12/Apr. 23, 1979. More specifically, in one embodiment of invention a cooperative biocide composition releases bromine with a concentration of released bromine in a body of water ranging from about 1 ppm to 2.3 ppm in the body of water in the presence of a silver ion in the body of water with a silver ion concentration ranging from about 1 ppb of silver ions to about 3 ppb of silver ions with the cooperative biocide combination effective to control microorganisms to thereby permit safe recreational use of the body of water with the released concentrations maintaining the level of harmful microorganisms below unacceptable levels specified in EPA DIS/TSS-12/Apr. 23, 1979.

The example includes the method of disinfecting a body of water with at least two biocides with at least one of the biocides maintainable at a lower concentration level when used in combination then if used alone with the released concentrations maintaining the level of microorganisms below the unacceptable levels specified in EPA DIS/TSS-12/Apr. 23, 1979. More specifically, the method includes releasing bromine into the body of water in sufficient amounts to maintain the bromine concentration in a range of about 1 ppm to about 2.3 ppm when in the presence of a concentration of silver ions in a range of about 1 ppb to about 3 ppb with the silver ions and the bromine effective to provided a disinfected body of water for recreational use with the level of harmful microorganisms below unacceptable levels specified in EPA DIS/TSS-12/Apr. 23, 1979.

Some examples of use include a spa, pool or other contained fluid for recreational use contains a body of water; a level of bromine present in the amount of 1 to 2.3 ppm; and a level of silver ions present in the amount of 1 to 3 ppb with the bromine and the silver ions cooperating to maintain a standard plate count of less than 200 colonies per milliliter and more specifically the bromine and the silver ions cooperating to maintain a standard plate count at 35 degrees F. of less than 200 colonies per milliliter.

The example of the method of treating a body of water is to add a N-halohydantoin derivative such as 1,3 dichloro-5,5 dimethylhydantion, 1,3 dibromo-5,5 dimethylhydantion or 1-bromo-3-chloro-5,5 dimethylhydantion to a body of water that includes a silver ion released a source of silver ions.

In further regards to examples of use the powder, granules, tablets/dipstick, and liquid produced from the silver chloride and DMH either in particulate or complex forms are of particular utility as biocidal agents for use in other environments that may not have been previously mentioned such as industrial as well as medical and home use applications including but not limited to elements of protective coatings such as paints, hand wash formulations, in ointments and related topical applications, cosmetics, cleaning and/or disinfectant/ sanitation products, toilet bowl cleaners, cooling towers, liquid paint, air washer systems, wastewater, pulp and paper processing operations, oil field applications, and decorative fountains and sanitation of recreational water such as swimming pools and spas. The DMH-silver chloride complex is also intended to be used as a component in coating fibers and filters.

If desired, the silver chloride and DMH and/or the DMH-silver complex can be formulated with suitable additives such as but not limited to binders, lubricants, disintegrants, and mold release agents. Other optional ingredients which may be used in the formation of a resultant product include fragrances, stabilizers, coloring agents, corrosion inhibitors, dyes, viscosity modifying agents, other biological agents, surfactants, effervescent, diluents, antifoaming agents, enzymes, anti-spotting agents, anti-oxidants, preservatives, and anti-corrosion agents, builders, chelating agents, and the like.

In order to verify that a compound containing a hydantoin ring, such as DMH, which has no known antimicrobial properties, interacts to increase the solubility of extremely insoluble silver, a test was performed using either silver chloride or silver bromide as the donor of metal ions in order to demonstrate the increase of silver concentration in a body of water when DMH is used in combination with the source of metal ions.

Figure 17:
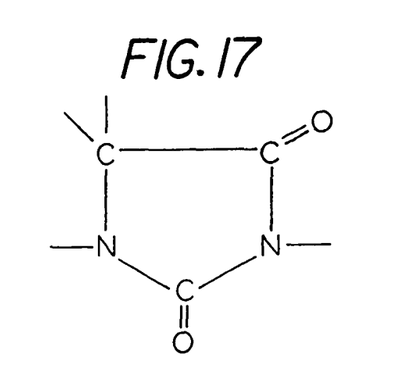
FIG. 17 shows the structure of a hydantoin ring.
Figure 18:
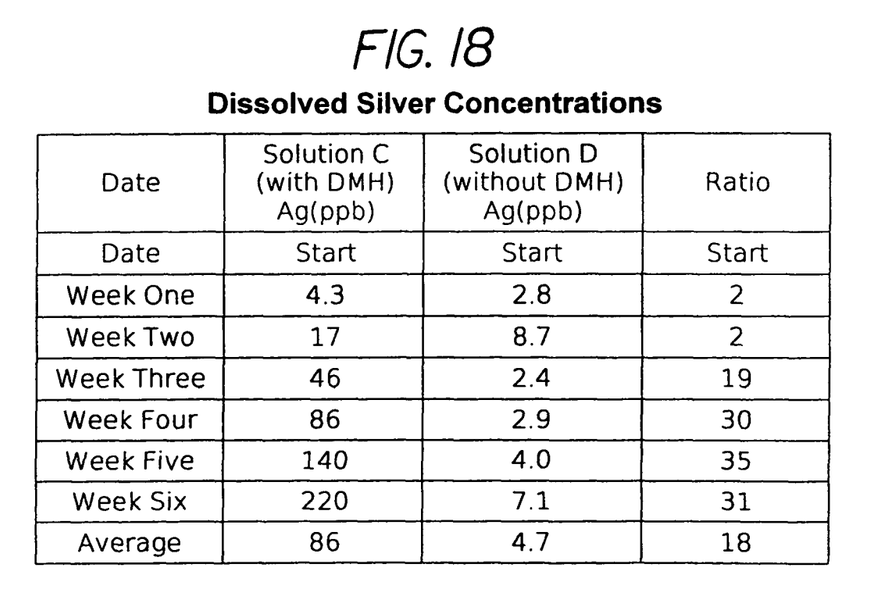
FIG. 18 shows the concentration of silver with and without a hydantoin.

FIG. 17 shows a schematic of the structure of a hydantoin ring with carbon and nitrogen atoms joined in a five-sided ring. An oxygen atom is attached to two of the carbons in the hydantoin ring. The lines extending from the third carbon atom and the nitrogen atom indicate that other atoms could be attached thereto. For example, in a compound containing a hydantoin ring, such as DMH (5,5-dimethylhydantoin), two methyl groups would be attached to the carbon atom an a hydrogen atom would be attached to each of the two nitrogen atoms.

It has been found that a compound containing a hydantoin ring such as 5,5-dimethylhydantoin (DMH), which lacks antimicrobial properties, has the ability to interact with a source of metal ions to increase the solubility of the silver in a water environment and enhance the antimicrobial process. It has also been found that compounds containing a hydantoin ring which have antimicrobial properties such as Bromochlorodimethylhydantoin (BCDMH) and Dichlorodimethylhydatoin (DCDMH) also interact to increase the solubility of silver in the presence of water. While a number of compounds with a hydantoin ring may be used as a practical matter one may want to avoid those compounds where the group or groups on the compound may have an adverse effect on the sanitized product.

Examples of other well known compounds wherein the compound contains a hydantoin ring include silverdimethyl-hydantoin 1-hydroxymethyl-5,5-dimethlyl hydantoin, glycolyurea and Copper hydantoin, Hydantoin-5-acetic acid, and Imidazolidines including parabanic acid, 2-Thiohydantoin, hydantoin purum, hydantoin, 1-Aminohydantoin hydrochloride,2-Imidazolidone, 2-Imidazolidone purum, 2-Imidazolidinethione, 2-hydrazino-2-imidazoline hydrobromide, 2-oxo-1-imidazolidinecarbonyl chloride, 1-methylhydantoin, 5-methylhydandtoin, 2-imidazolidone-4-carboxylic acid, allantoin, allantoin purum, creatinine anhydrous, creatinine biochemika, creatinine hydrochloride, 2-methyl-2-imidazoline, 2-methylithio-2-imdazoline hydrodide, 3-bromo-1-chlor-5-5-dimethlyhydantoin, 1-3-dibromo-5,5-dimethly hydantoin purium, 1-3-dichlorol-5,5-dimethylhydantoin, 1,3-dichlor-5,5-dimethylhydantoin, hydantoin-5-acetic acid. 2-chlorocarbonyl-1-methanesulfonyl-2-imidazolidinone. 5.5-dimethylhydantoin purum. 5,5-dimethylhydantoin, 2-imino-1-imidaolidineacetic acid, 1,3-dimethyl-2-imidazolidinone puriss, 1,3-dimethly-2-imidazolidinone purum, 1,3-dimethyl-2-imidazolidinone, 1-(2-hydroxyethyl)-2-imdazolinone, 1,5,5-trimethlylhydantoin, 5-ethyl-5-methylhydantoin, 2-phenyl-2-imidazoline purum, 2-(4,5-dihydro-1h-imidazoyl)-2-phenol, 4-(4,5-dihydro-1H-imidazol-2yl)phenylamine, 5-methyl-5-phentylhydantoin, 2-benzylimidazoline, 4-(4-methyl-4,5-dihydro-1H-imidazol-2-yl)phenyl, Imidazolidinyl urea, 4-hydroxymephenytoin, triethoxy-3-(2-imidazolin-1-yl)propysiliane purum, 1,(p-tosyl)-3,4,4-trimethylimidazolidine, naphazoline nitrate purisss, 5,5,diphenyl-2-thiohydantoin, 5-(4-hydroxyphenyl)- 50 phenylhydantion, 5-(p-methylphenyl)-5-phenyhydantoin, 1,3,bisbensyl-2-oxoimidazoline-4,5-dicarboxylic acid. Other examples of hydantoins are listed in European patent EP0780125 which is herby incorporated by reference. The above list compounds with a hydantoin ring is illustrative and no limitation thereto is intended.

A silver ion donor in the presence of a compound containing a hydantoin ring such as DMH has a level of free silver higher than anticipated when compared to the silver ion donor in a water environment without the DMH. The results suggest that DMH enhances the solubility of the silver thereby increasing the biocidal effectiveness.

In order to verify that a compound containing a hydantoin ring, such as DMH, interacts to increase the solubility of insoluble silver in a water environment, a test was performed using either silver chloride or silver bromide as the donor of silver metal ions. The test demonstrated the enhancement of silver in a water environment when DMH is used in combination with a source of silver ions.

Example 4

Silver bromide was initially prepared from a saturated sodium bromide solution, combined with silver nitrate in solution. The yellow precipitate, silver bromide, was than purified by filtration and washing. Additionally, the solid was allowed to dry before use.

A buffer system having a pH of 7.41 was prepared by adding Fisherbrand® potassium phosphate monobasic-sodium phosphate dibasic buffer to 2 Erlenmeyer flasks filled with 1000 mL of purified water. The first flask was treated with 1.12 grams of 5,5-dimethylhydantoin (DMH) and marked solution "C" (with DMH) and the second flask was left untreated and marked solution "D" (without DMH) for control. In regards to the 5,5-dimethylhydantoin (DMH), the 5,5-dimethylhydantoin (DMH) comprised 97% reagent grade was obtained from Aldrich® (CAS No. 77-71-4, Cat. No. D161403-1KG).

After the initial set-up, approximately 0.10 grams of dried silver bromide was introduced into a dialysis tubing (Fisherbrand®, 45 mm, MWCO 12,000-14,000) along with purified water. The ends of the dialysis tubing were clamped to contain the silver bromide and purified water. Next, the outside of the dialysis tubing was rinsed several times to ensure that silver bromide residue was not on the outside of the dialysis tubing. A string was then tied to one clamp, and one tube was introduced into each flask. A magnetic stir bar was used to mix the solutions.

During the period of the test, a 100 mL sample were removed from solution "D" (without DMH) and solution "C" (with DMH) at weekly intervals and analyzed for their pH using Orin Perphect Meter 370 and analyzed for their silver ion concentrations using atomic absorption spectrometry.

FIG. 9 shows a table containing a list of the dissolved silver concentration, in parts per billion (ppb) obtained from the 100 mL samples for solution "D" (without DMH) and solution "C" (with DMH) at each of their respective weekly time intervals. The average concentration of dissolved silver for solution "C" (with DMH) was 86 ppb while solution "D" (without DMH) had an average concentration of dissolved silver of 4.7 ppb.

A week after the start date, the concentration of dissolved silver for solution D (without DMH) was at 4.3 ppb, while the concentration of dissolved silver for solution C (with DMH) was at 2.8 ppb. By the end of the testing, 6 weeks later, the concentration of dissolved silver for solution C (with DMH) had increase to 220 ppb, while the concentration of dissolved silver for solution D (without DMH) was 7.1 ppb. That is, by the end of the 6 weeks test, the concentration of dissolved silver was at least 30-fold greater in solution C (with DMH) then for solution D, (without DMH).

In summary, the results of the above testing confirmed that in a solution containing silver bromide, the presence of compound containing a hydantoin ring, such as DMH, leads to a higher dissolved silver concentrations than compared to a control solution containing silver bromide without the presence of the DMH. These results suggest that compounds containing a hydantoin ring interact with silver to form a soluble complex even if the source of silver comprises an extremely insoluble silver salt such as silver bromide.

In regards to generating a level of silver ions, the King Technology, Inc. Frog® Mineral Cartridge provides one method of delivering silver ions in the form of solid silver chloride (AgCl) distributed over a porous matrix. The water releases the soluble silver ions into the water environment with. DMH resulting in the formation of ionic-hydantoin structures. It would be anticipated that soluble silver ions would be depleted from the water environment through the formation of silver bromide, an insoluble salt. However, as shown in FIG. 2 after the DMH was added to the water environment, the actual silver concentrations were higher than the calculated theoretical silver concentration.

It is noted that various insoluble or slightly soluble transition metal salts may also be used in the present invention as a source of silver ions. Examples of insoluble or slightly soluble transition metal salts suitable for use in the present invention include, but are not limited to, AgCl, AgBr, AgI, $Ag_2S$, $Ag_3PO_4$, $NaAg_2PO_4$, CuS, and $NaCuPO_4$. Other examples of silver compounds include, but are not limited to, $AgNO_3$, $Ag_2CO_3$, AgOAc, $Ag_2SO_4$, $Ag_2O$, $[Ag(NH_3)_2]Cl$, $[Ag(NH_3)_2]Br$, $[Ag(NH_3)_2]I$, $[Ag(NH_3)_2]NO_3$, $[Ag(NH_3)_2]_2SO_4$, silver acetoacetate a silver benzoate, a silver carboxylate, silver amine complexes such as $|Ag(NR_3)_2|X$, where R is an alkyl or aryl group or substituted alkyl or aryl group and X is an anion such as, but not limited to, $Cl^-$, $Br^-$, $I^-$, $OAc^-$, $NO_3^-$ and $SO_4^{2-}$.

Although the use of the silver ion donor such as silver, silver oxide, silver salt, or a combination thereof have been disclosed, various types of silver alloys may also be used. The silver may be used standing along in its pure/elemental or alloyed form or coated or impregnated to a substrate and placed in compartment 28. In addition, other types of silver ion donors, other types of transition metals, transition metal oxides, or a combination thereof, and other alternative bactericides whose solubility can be changed in the presence of a compound containing a hydantoin ring can also be used in the present invention.

As can be seen from the above tests that one may further enhance the disinfecting of the wash product by using a halogen such as chlorine or bromine in conjunction with the source of silver ions and the hydantoin. In such cases the level of halogen can be maintained at a lower level than if the halogen were used alone since both the available silver ions and the halogen can cooperatively disinfect an article As used herein the term conventional washing machine also includes dishwashing machines that rely on agitation of the water by spraying water containing the detergent on the utensils to remove unwanted soil from the utensils with the dishwashing machine lacking any separate feature for disinfecting the utensils.

I claim:
1. A laundry product for simultaneous cleaning and sanitizing a batch of soiled laundry by addition of the laundry product to a conventional washing machine, wherein the laundry product is a both a cleaning and sanitizing agent when in the presence of a body of water, with the laundry product consisting of:
   a) a water activeable laundry detergent in solid, liquid or gel form for releasing soil from the batch of soiled laundry when the water activeable laundry detergent is present in the body of water with the batch of soiled laundry; and
   b) a disinfectant composition consisting of:
      i) a non-disinfectant hydantoin; and
      ii) silver chloride for normally releasing and maintaining a first level of silver ions in the body of water, wherein the non-disinfectant hydantoin and silver chloride are intermixed for simultaneous dispensing into the washing machine, and wherein the non-disinfectant hydantoin increases the level of available silver ions in the body of water to a level that is greater than the level of silver ions normally available if the silver chloride is used without the hydantoin, such that the disinfecting capacity of the laundry product is enhanced as the soiled laundry is being agitated in a washing machine.

2. The laundry product of claim 1 wherein the laundry detergent, the silver chloride, and the non-disinfectant hydantoin are intermixed for simultaneous dispensing into a conventional washing machine.

3. The laundry product of claim 2 wherein the laundry detergent, the silver chloride and the non-disinfectant hydantoin are in tablet form.

4. The laundry product of claim 2 wherein the non-disinfectant hydantoin has a concentration of at least 5 ppm in the body of water and the level of available silver ions is in excess of 2 ppm. level of available silver ions in the body of water to thereby increase the disinfecting capacity of the wash product.

5. A wash product for simultaneously cleaning and sanitizing a batch of soiled articles by addition of the wash product to a washing machine having a wash cycle wherein the wash product contains both a washing agent and a sanitizing agent comprising:
   a) a water activeable detergent for releasing unwanted residue from the batch of soiled articles when the water activeable detergent is in contact with the batch of soiled articles and a body of water; and b) a disinfectant composition comprising:
  i) a non-disinfectant hydantoin; and
  ii) a chemical source of silver ions for normally maintaining a first normal level of available silver ions in the body of water, wherein the hydantoin and the source of silver ions cooperatively increase the disinfecting capacity of the wash product by increasing the level of available silver ions in the body of water to a level that is greater than the level of silver ions normally available if the silver ion source is used without the hydantoin, such that the disinfecting capacity of the wash product is enhanced.

6. The wash product of claim 5 wherein the water activeable detergent, the hydantoin and the source of silver ions are intermixable solids storable as a composition in a ready to use state and the hydantoin may or may not contain an antibacterial agent.

7. The detergent product of claim 5 wherein the hydantoin comprises DMH and the chemical source of silver ions comprise silver chloride or nano silver particles.

8. The wash product of claim 5 wherein the detergent is in gel, solid or liquid form and the hydantoin having a concentration of at least 5 ppm in the body of water.

9. A detergent and sanitizing product composition for cleaning and sanitizing a batch of soiled articles comprising:

a) a standalone detergent for removing unwanted materials from the batch of soiled articles when the batch of articles are in water contact; and b) a standalone sanitizer comprising:
  i) a non-disinfectant hydantoin, and
  ii) a source of silver ions wherein the standalone sanitizer and the standalone detergent are intermixable with each other in a body of water in a washing machine to enable simultaneous washing and sanitizing of the batch of soiled articles during a washing cycle, and wherein the hydantoin and the source of silver ions cooperatively increase the disinfecting capacity of the wash product by increasing the level of available silver ions in the body of water to a level that is greater than the level of silver ions normally available if the silver ion source is used without the hydantoin.

10. The detergent and sanitizing product composition of claim 9 wherein the hydantoin comprises DMH and the source of silver ions comprises silver chloride and the standalone detergent is either a solid, a liquid or a gel.

11. The detergent and sanitizing product of claim 10 wherein the source of silver ions comprises silver chloride and the presence of the hydantoin maintains the level of silver ions in excess of 2 ppm in the body of water when the silver chloride and the hydantoin are placed in a washing machine containing the batch of soiled articles.

12. The detergent and sanitizing product composition of claim 10 wherein the hydantoin has a concentration of in excess of 5 ppm in the body of water.

13. A method of simultaneously washing and disinfecting a batch of soiled articles in a conventional washing machine comprising the steps of:

a) placing the batch of soiled articles into the conventional washing machine;

b) dispensing a wash product containing a detergent, a source of silver ions and a non-disinfectant hydantoin into the washing machine; and c) initiating a wash cycle to activate the wash product through agitated water contact of the wash product and the batch of soiled articles; wherein the wash product is enabled to both wash and disinfect the batch of articles during a washing cycle of the conventional washing machine, as the source of silver ions releases silver ions into the washing machine with the hydantoin increasing the level of silver ions available in the body of water by increasing the solubility of silver ions in the body of water, such that the silver ions are present at a level that is greater than the level of silver ions normally available if the source of silver ions is used without the hydantoin.

14. The method of claim 13 wherein the source of silver consists of silver chloride or nano silver particles and the hydantoin consists of dimethyl hydantoin and a level of available silver ions in the washing machine is in excess of 2 ppm.

15. The method of claim 13 wherein the washing machine is a clothes washer and the clothes washer contains an agitator for agitating the clothes during the washing cycle.

16. The method of claim 15 wherein the batch of soiled articles are immersed in a body of water in the clothes washer.

17. The method of claim 14 wherein the batch of soiled articles are sprayed with water containing the wash product.

18. The method of claim 14 wherein the washing and disinfecting of the batch of soiled articles occurs simultaneously during the washing cycle.

* * * * *